(12) United States Patent
Rajagopal et al.

(10) Patent No.: US 9,480,426 B2
(45) Date of Patent: Nov. 1, 2016

(54) METHODS AND SYSTEMS FOR EXCHANGING SIGNALS WITH MEDICAL OR PHYSIOLOGICAL INSTRUMENTATION

(71) Applicant: CALIFORNIA INSTITUTE OF TECHNOLOGY, Pasadena, CA (US)

(72) Inventors: Aditya Rajagopal, Irvine, CA (US); Axel Scherer, Barnard, VT (US); Akram Sarwat Sadek, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 277 days.

(21) Appl. No.: 14/153,819

(22) Filed: Jan. 13, 2014

(65) Prior Publication Data

US 2014/0221799 A1    Aug. 7, 2014

Related U.S. Application Data

(60) Provisional application No. 61/761,591, filed on Feb. 6, 2013.

(51) Int. Cl.
  *A61B 5/1455*   (2006.01)
  *A61B 5/1459*   (2006.01)
  *A61B 5/00*     (2006.01)

(52) U.S. Cl.
  CPC .......... *A61B 5/1459* (2013.01); *A61B 5/0031* (2013.01); *A61B 5/14552* (2013.01); *A61B 5/6867* (2013.01); *A61B 2560/0219* (2013.01)

(58) Field of Classification Search
  CPC  A61B 5/1455; A61B 5/1459; A61B 5/6867; A61B 5/0031; A61B 5/14551; A61B 5/14552; A61B 2560/0219
  See application file for complete search history.

(56) References Cited

U.S. PATENT DOCUMENTS

| | | | |
|---|---|---|---|
| 8,145,286 B2* | 3/2012 | Arai ................... | A61B 5/14532 600/316 |
| 2005/0187438 A1* | 8/2005 | Xie .................... | A61B 5/14532 600/310 |
| 2011/0044694 A1* | 2/2011 | Scherer ............... | A61B 5/6867 356/300 |

* cited by examiner

*Primary Examiner* — Eric Winakur
(74) *Attorney, Agent, or Firm* — Steinfl & Bruno, LLP

(57) ABSTRACT

A process is described for testing a biomedical property of an internal tissue of a patient. Optical energy emitted by an external source is transferred through a nail of the patient to an instrument device implanted beneath the nail. A portion of the transferred optical energy is converted to electrical power for driving components of the implanted instrument. Using the electrical power, a characteristic of the internal tissue associated with the measurement of the biomedical property is sensed and an optical signal based on the sensed characteristic is transmitted through the nail to an external data reader.

39 Claims, 11 Drawing Sheets

Example System 600

Typical Fingernail cross-section 10

Typical Nail Optical Refraction 20

Typical Nail Absorption Coefficient vs. λ 25

Example Implant 30

Example Lensatic Implementation 40

Example Waveguide 50

Example Surgical Procedure 80

Placing a Biomedical Test Instrumentation Device within a Body of a Patient:

81
Open an access through a fingernail or toenail ("nail") of the patient to a nail bed beneath the nail wherein the nail bed has a capillary carrying blood and a nerve

82
Implant the biomedical test instrument below the nail via the opened access, wherein the test instrument is placed in proximity with the nail bed and operable for sensing a biomedical characteristic of the blood or the nerve and transmitting an output optical data signal based on the sensed biomedical characteristic to an optical data reader, which is disposed external to the body of the patient, and wherein the implanted biomedical test instrument is configured for converting optical energy received through the nail from a light source, which is disposed external to the body of the patient, into power for driving the sensing the biomedical characteristic and the transmitting the output signal

83
Install a passive optical device onto an upper outer surface of the nail for directing the optical energy from the external light source to the implanted biomedical device through the nail (optional)

Fig. 8

Example Process 90

Energizing a Biomedical Instrument Device Disposed within the Body of a Patient:

---

91
Transferring optical energy emitted by an external source through a nail of the patient to the biomedical instrument device, which is implanted beneath the nail

---

92
Convert the optical energy absorbed by the implanted biomedical instrument device to electrical power wherein, energized by the electrical power, the biomedical instrument is operable for sensing a characteristic of a tissue of the patient and for transmitting an optical output signal based on the sensed tissue

METHODS AND SYSTEMS FOR EXCHANGING SIGNALS WITH MEDICAL OR PHYSIOLOGICAL INSTRUMENTATION

CROSS REFERENCE TO RELATED APPLICATIONS

The present Application claims priority to related U.S. Provisional Patent Application No. 61/761,591 filed 6 Feb. 2013 which is incorporated by reference in its entirety.

FIELD

Embodiments of the present disclosure relate generally to medical and physiological instrumentation. More particularly, an example embodiment of the present disclosure relates to signaling medical and physiological instruments.

BACKGROUND

Instrumentation is used widely for accessing blood and other target physiological tissues, structures or organs and gathering information therefrom for medical and scientific purposes. Instrument components of these instrumentation include miniature electronic and electromechanical devices or microsystems, which may be implanted or otherwise disposed within the body of a patient or biological specimen in proximity to the target tissue, structure, or organ for direct (or close) contact therewith. As they perform their operations, such devices consume energy.

Finite power supplies for these devices, such as batteries, must be replaced or recharged upon inevitable exhaustion of their available energy, which with implants entails at least some level of unwanted invasiveness. Batteries also add undesirable size and weight to the device, and depending upon their chemical composition and packaging, may introduce medical or biological risk with implant use. Powering the implanted devices through leads, conduits, or the like from an external power source however entails undesirable penetration of the patient or specimen and varying levels of associated discomfort, inconvenience and possibly a risk of infection.

More recently, implanted medical and physiological (hereinafter "medical") instrumentation components have included wireless microsystems. Such wireless microsystems are powered and exchange data signals or otherwise communicate with "outside world" instrument components, disposed external to the patient or specimen, outside of the body of the patient or specimen (hereinafter "patient") in which the implanted microsystem device is disposed.

For example, power may be supplied to an implanted wireless microsystem from an external power source by electrical induction using magnetically coupled transformer coils. An external coil is brought into proximity and alignment with a coil implanted within the body of the patient. Power may be supplied to the implanted wireless microsystem upon attaining a critical coupling, in which the coil of the external source supplies power inductively to the implant coil.

While the implant may be thus powered, the inductive coupling may be operable at frequencies too low to support efficient intercommunication at modern data rates. Further, the implanted coil occupies space and weight in vivo, which may entail unwanted invasiveness and discomfort.

"Radio communications" may also be used in which power supply and data exchange interactions with the implanted microsystem are made at microwave frequencies from an external radio frequency (RF) source. The signal exchange transactions with the microsystem and its power supply entail coupling via an antenna sub-component implanted therewith.

The implanted antenna, however, also occupies space and weight in vivo and may further entail some degree of undesirable microwave bioexposure during its operation. Optical communications may mediate or ameliorate some of these instrumentation related issues discussed above.

Optical communication using lasers or light-emitting diodes (LEDs) may allow signal interchange with implanted medical instruments as well as power supply thereto. For example, a laser or LED light source and associated photodetector external to the body of the patient may transact or otherwise exchange data signals with a phototransceiver component of an implanted microsystem and/or provide power to a photovoltaic-driven power generation component thereof.

However, significant issues remain to be overcome relating to optical scattering and absorption and other optical characteristics of biological tissue, structures, organs, and fluid filled vessels in or near where the instrument may be implanted and/or between the instrument and the light source for some practical implementations of powering implanted medical or physiological instruments or exchanging data signals therewith optically.

Power and signal transfer through human skin may be subject to significant loss by optical scattering in epithelial tissue and optical absorption by melanin and other pigments and substances. Transcutaneous optical communication and power transfer systems demand additional power to cover such losses.

Moreover, the thickness of tissue between capillaries at which detector components may be disposed at the skin surface typically exceeds one millimeter. At this thickness, however, handling the optical transceiver (power supply and reader) component in place for proper alignment to preserve sufficient optical coupling becomes challenging.

For example, optical power levels demanded from an incident laser or LED source for driving sufficient on-chip operating currents and voltages on the implanted instrument component may exceed tissue damage thresholds. Pulsed optical drivers for overcoming this power transfer issue add complexity and expense, while possibly partially reducing reliability.

Approaches described in this section may or may not have been conceived or pursued previously. Unless otherwise indicated, it should not be assumed that any approaches discussed above include any alleged prior art merely by any such discussion. Not dissimilarly, any issues discussed in relation to any of these approaches should not be assumed to have been recognized in any alleged prior art merely based on any such discussion above.

SUMMARY

It would be useful to efficiently provide power and/or exchange signals wirelessly from an external optical energy source to medical and physiological instrument components implanted within the body of a patient or biological specimen without significant scattering or absorption losses. It would also be useful to achieve this benefit with optical energies that do not rise to a threshold of physiological damage and without added alignment requirements. Further, it would be useful to achieve these benefits without added costs and complexity, or reduced reliability.

Example embodiments of the present disclosure are operable for efficiently providing power to medical and physiological instrument components implanted within the body of a patient or biological specimen, and exchanging signals therewith, wirelessly using an external optical energy source without undue scattering or absorption losses. Example embodiments achieve this benefit with sufficient in situ optical alignment at optical energies below the threshold of physiological damage. Further, embodiments of the present disclosure achieve these benefits without adding costs and complexity, or reducing reliability over typical conventional levels.

An example embodiment of the present disclosure uses light at optical wavelengths as an information and power transfer medium for medical and physiological instrumentation devices implanted within a patient or physiological specimen. Photovoltaically driven power generator components provide energy for operating electronic circuits, other optically driven components such as micro- and nanomachines, implanted secondary optical sources, spectroscopy systems, glucometers and other instruments operable for gathering medical and physiological (hereinafter "medical") data from within a patient or specimen (hereinafter "patient"). Light energy is provided from an external light source to a wireless sensor implanted within the patient without optical absorption or scattering over its path at levels sufficient to undo its transfer.

An example embodiment of the present disclosure relates to a process for testing a biomedical property of an internal tissue of a patient. Optical energy emitted by an external source is transferred through a nail of the patient to an instrument device implanted beneath the nail. A portion of the transferred optical energy is converted to electrical power for driving components of the implanted instrument. Using the electrical power, a characteristic of the internal tissue associated with the measurement of the biomedical property is sensed and an output data signal based on the sensed characteristic is transmitted through the nail to an external data reader.

Therefore, an example embodiment of the present disclosure is operable for efficiently providing power to medical and physiological instrument components implanted within the body of a patient or biological specimen, and exchanging signals therewith, wirelessly using an external optical energy source without undue scattering or absorption losses. Example embodiments thus achieve this benefit with sufficient in situ optical alignment at optical energies below the threshold of physiological damage. Further, embodiments of the present disclosure thus achieve these benefits without adding costs and complexity, or reducing reliability, over typical conventional levels.

BRIEF DESCRIPTION OF THE DRAWINGS

Example embodiments of the present disclosure are described below in relation to efficiently providing power to medical and physiological instrument components implanted within the body of a patient or biological specimen, and exchanging signals therewith, wirelessly using an external optical energy source without undue scattering or absorption losses. The description below refers to the flowing drawing figures, in which:

FIG. 8 depicts a flowchart for an example surgical procedure for placing a biomedical test instrument device within the body of a patient, according to an embodiment of the present disclosure;

FIG. 9 depicts a flowchart for an example process for energizing a biomedical instrument device disposed within the body of a patient, according to an embodiment of the present disclosure.

Figure 2A:
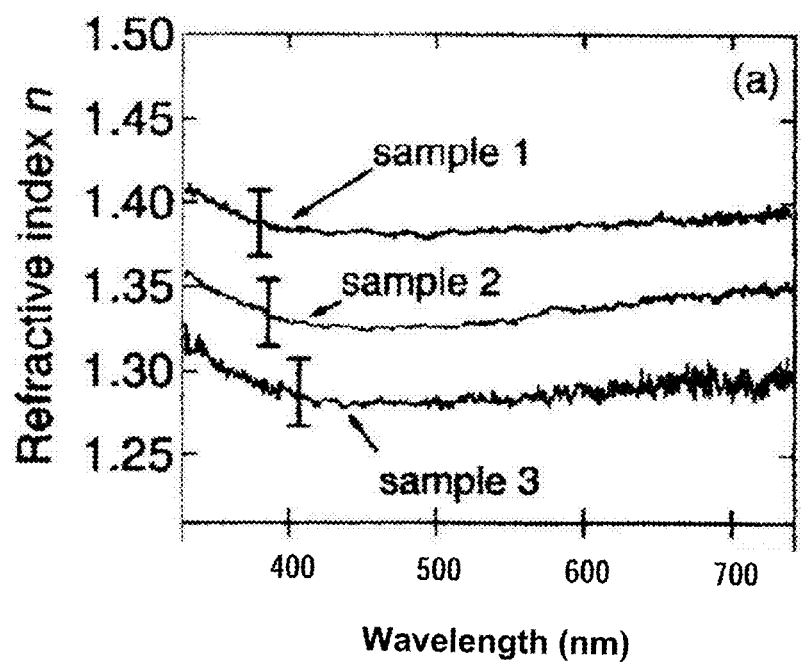
FIG. 2A depicts absorption characteristics of three typical nail samples as a function of optical wavelength.
Figure 2B:
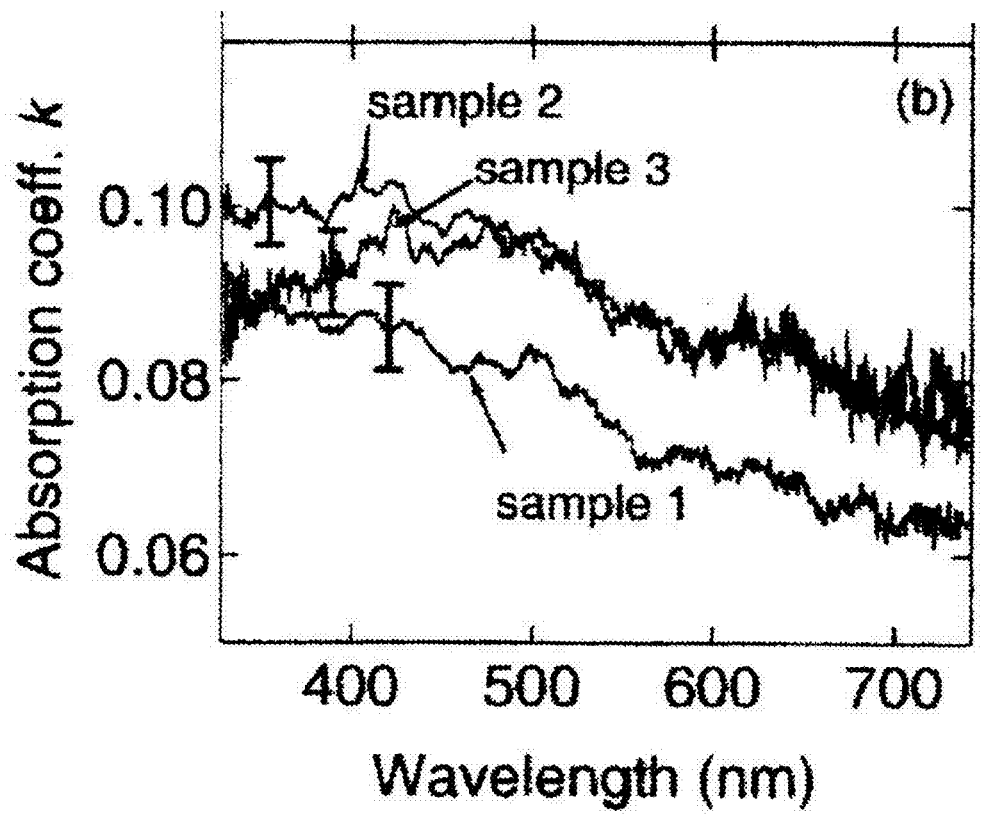
FIG. 2B depicts the refraction characteristics of three typical nail samples as a function of optical wavelength.

No scale applies in these drawings unless and except as specifically stated, as with reference to the vertical axis and the horizontal axis shown in each of FIG. 2A and FIG. 2B.

DESCRIPTION OF EXAMPLE EMBODIMENTS

Providing power to medical and physiological instruments and exchanging signals therewith are described herein. In the following description, for the purposes of explanation, numerous specific details are set forth in order to provide a thorough understanding of the present disclosure. It will be apparent, however, that embodiments of the present disclosure may be practiced without these specific details. In other instances, well-known structures and devices are not described in exhaustive detail, in order to avoid unnecessarily obfuscating, obstructing, obscuring, or occluding aspects of the present disclosure.

Overview

An example embodiment of the present disclosure is described below in relation to a process for testing a biomedical property of an internal tissue of a patient. Optical energy emitted by an external source is transferred through a nail of the patient to an instrument device implanted beneath the nail. A portion of the transferred optical energy is converted to electrical power for driving components of the implanted instrument. Using the electrical power, a characteristic of the internal tissue associated with the measurement of the biomedical property is sensed, and an output data signal based on the sensed characteristic is transmitted through the nail to an external data reader.

An example embodiment of the present disclosure uses light at optical (infrared, visible, ultraviolet) wavelengths as an information and power transfer medium for medical and physiological instrumentation devices implanted within a patient or physiological specimen. Photovoltaically driven power generator components provide energy for operating electronic circuits, other optically driven components such as micro and nanomachines, implanted secondary optical sources, spectroscopy systems, glucometers and other instruments operable for gathering medical, hematological, pharmaceutical, physiological and biochemical (hereinafter individually and collectively "biomedical") data from within a patient or specimen (hereinafter "patient"). Light energy is provided from an external light source to a wireless sensor implanted within the patient without optical absorption or scattering over its path at levels sufficient to undo its transfer.

Example Biomedical Instrumentation Devices

Figure 1:
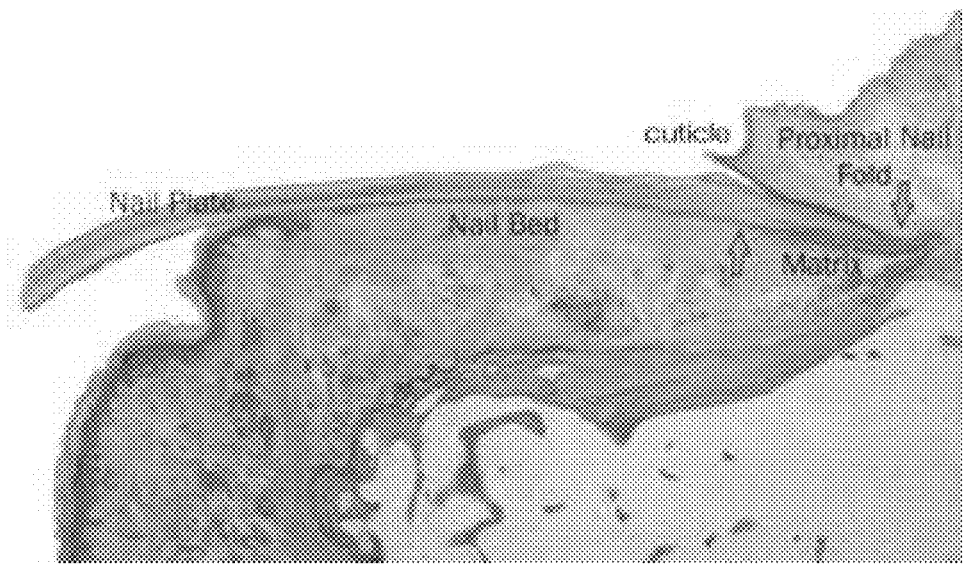
FIG. 1 depicts a typical human fingernail in cross-section.

FIG. 1 depicts a typical human fingernail in a cross-section 10. An example embodiment of the present disclosure may be implemented in relation to a glucometer or other medical/physiological ("biomedical") instrument. The example glucometer is operable for detecting a level of blood glucose from within the patient and transmitting data related to the detected glucose level to a component external to the patient. For example, a glucometric instrument component 11 may be placed beneath the nail and in proximity to capillaries of the fingertip. In this location, the glucometric detector 11 potentiometrically detects the blood glucose concentration of the patient.

An external optical power source 12 introduces light to drive a photovoltaic cell 13, which generates electrical power on-chip to perform the potentiostatic measurement related to the detection of the glucose level. The resulting measured blood glucose reading is then transmitted from within the patient using a light source 14 "on-chip" in relation to the detector 11 and its power generator 13. The on-chip light source 14 thus relays the detected glucose level measurement to an external reader 15, such as a photosensitive diode or another photodetector, e.g., proximate to or disposed with the external light source 12.

Example embodiments of the present disclosure relate to providing power to implanted medical/physiological devices, and exchanging signals therewith optically over at least partially transparent (or translucent) and substantially scatter-free paths from the external source 11/reader 15 over optical pathways in the fingernails or toenails. FIG. 2A depicts absorption characteristics 20 of three typical nail samples as a function of optical wavelength. FIG. 2B depicts the refraction characteristics 25 of three typical nail samples as a function of optical wavelength.

As shown in FIG. 2A and FIG. 2B, human fingernail tissue typically has a relatively high refractive index 'n' of from approximately 1.40-to-1.45, combined with relatively low absorption losses, which correspond to absorption coefficients 'k' between 0.06 $cm^{-1}$-to-0.10 $cm^{-1}$, each over a range of optical wavelengths from approximately 400 nanometers (nm) to 700 nm. Moreover, the stiff nature of fingernails and toenails enables the rigid adhesive or other mounting of source component 11 and reader 15 to the outside of the patient's body on the nail surface in permanent (or near permanent) optical alignment of these devices with the implanted microsystem.

Figure 3:
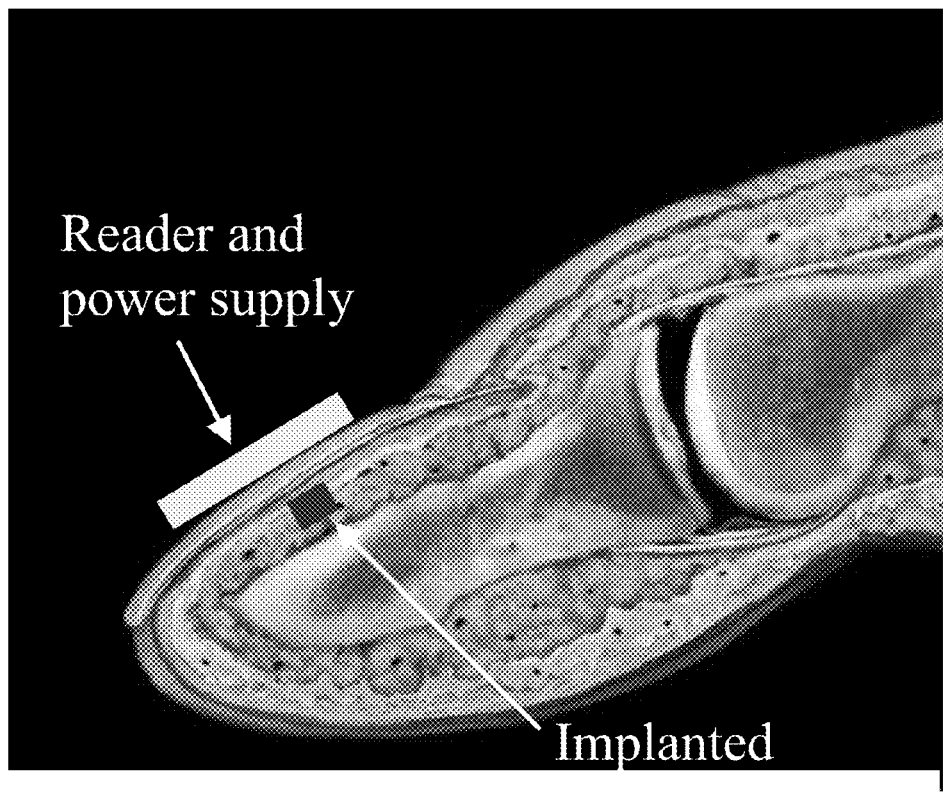
FIG. 3 depicts an example instrumentation system in situ, according to an embodiment of the present disclosure.

FIG. 3 depicts an example instrumentation system 30 in situ, according to an embodiment of the present disclosure. In an example embodiment of the present disclosure, a microscopic wireless instrument component 31 is implanted surgically below the nail. A reader and power supply component 32 is fastened to an upper outer surface of the nail.

The instrument component 31 may be injected laterally underneath the nail or by drilling perpendicularly through the nail from an upper, outer surface thereof. With drilled implantations of the instrument component, nail material removed by the drilling can be replaced with a material such as nail polish, which absorbs less light than the keratin based nail material and thus provides a more transparent waveguide pathway with a high refractive index. The size of particular wireless instrument component implants 31 may make their injection preferable, as they may thus be located precisely within the tissue of the nail-pad below the bottom inner surface of the nail.

Light may be waveguided through the nail to instrument components implanted by insertion at the distal end of the nail bed, just proximal to the hyponychium. Implantation at the distal end of the nail bed just proximate to the hyponychium minimizes the amount of tissue that must be dissected, simplifying the implant surgery relative to other approaches and minimizing postoperative pain and risks related to infection, complications or surgical failure. Implantation of the instrument component further proximally may increase risks related to scarring and subsequent retraction of the nail from the nail bed as the nail grows over the nail bed. Alternatively or additionally, a hole may be drilled to penetrate the nail, through which the instrument component may be inserted. Upon insertion, the implanted instrument component may subsequently be covered with appropriate material.

The nail itself protects the instrument component inserted beneath it and its rigidity provides a stable platform to which optical power supply and signal exchange components can be fastened. Moreover, its low optical scattering and absorption characteristics allow efficient power and signal transfer through the nail material without the significant losses characteristic of epidermal skin tissue, which is also generally unsuited to affixing optics or electronics useful for the optical power supply and signal exchange. The hardness characteristics of the nail tissue enables the construction of relatively complex optical systems to semi-permanently interface with the wireless instrument component 31 inserted underneath the nail with the reader and power supply component 32 on top of the nail.

An example embodiment may be implemented in which optics and electronics component 32, for power transfer and signal exchange with instrument components 31 inserted below the nail, are fastened to the rigid upper surface of the nail with commercially available materials commonly used for cosmetic or artificial nail extensions and/or other biocompatible adhesion materials. Such materials are typically tested to various standards associated with the pharmaceutical and cosmetic industries and are well characterized as generally avoiding discomfort, rash formation and/or other tissue irritations typical of contacts taped or glued to the skin.

Figure 4:
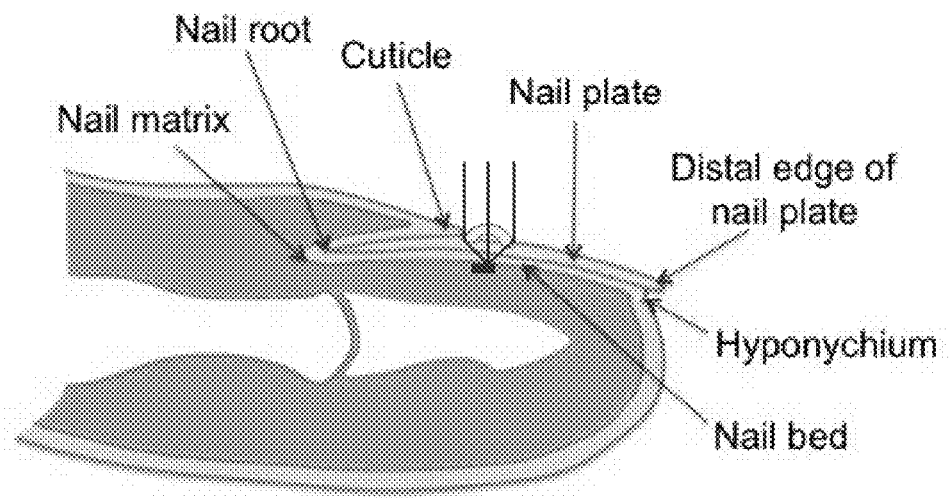
FIG. 4 depicts an example lens component of the instrumentation system, according to an embodiment of the present disclosure.

FIG. 4 depicts an example lens component 44 of the instrumentation system 30, according to an embodiment of the present disclosure. For optical power transfer from an external source to an implanted instrument component or an exchange of optical signals therewith, light energy may be guided and/or focused by optically transmissive media disposed over the external nail surface or embedded, at least partially, within the nail.

An example embodiment may be implemented in which one or more lenses and/or waveguides are disposed over a top, upper surface. A lens/waveguide may be constructed using a substantially transparent, non-absorbing and non-scattering material such as a nail polish. Alternatively or additionally, a lens/waveguide may be fashioned or crafted surgically, by embossing or machining structures into the nail material, and/or by techniques and methods similar to those used by opticians and other artisans of ordinary skill in optical technologies. Surgical procedures and other techniques related to crafting lenses/waveguides into nail material are substantially painless and free of infection risks.

Light energy from an optical power/signal source 45 over the upper surface of the nail (e.g., mounted thereon) may thus be focused on a photovoltaically active portion of the implanted instrument component 31 and optical signals may be exchanged as directed by the lens/waveguide 44 between a signal source and reader mounted on the top of the nail and the implanted instrument component.

For example, an infrared laser may be used to power the wireless implant with photovoltaic collectors mounted on the microchip with which the implanted instrument component is implemented. Surgical micromachining procedures over the upper surface of the nail may be used for accurate optical alignment of the laser and the photovoltaic collector systems. Fresnel, hemispherical and convex lenses may be crafted by techniques familiar to opticians and other optical artisans for the focusing of the laser beam onto the small region of the implanted instrument chip related to the photovoltaic energy collector sub-component thereof.

An example embodiment may be implemented in which the infrared laser is glued, essentially permanently, onto the outer surface of the nail. The position of the laser and associated signal source/reader may be adjustable and/or shifted over time to compensate for nail growth, reduction of swelling in the phalanges associated with healing or other processes (or conversely, for inflammation) and shifting positions of the externally mounted component associated therewith.

In an example embodiment of the present disclosure, the implanted instrument component is embedded into the nail itself. The instrument component embedded in the nail is optically powered by an external power source and exchanges optical signals with an external signal transceiver, source/reader or the like.

An example embodiment may be implemented in which the instrument component embedded in the nail is operable for performing a spectroscopic measurement over blood, which is present within the array of capillaries within the nail bed directly underneath the nail. As the nail grows out from the digit over time, the embedded instrument component is removed, ejected and disposed from the patient's body, which allows replacement or upgrade of the implant instrument component without surgical intervention beyond the nail itself.

Optical structures may be constructed or adjusted using a material such as a substantially transparent nail polish on the surface of the nail. Typical commercially available cosmetic type nail polishes have a refractive index n of approximately 1.5. Used as an optical structure or adjunct in implementing an example embodiment of the present disclosure, nail polish effectively enables the efficient mode-matching of light energy through the nail to the implanted instrument component.

Grits or similar materials of selectively engineered sizes may be added in various concentrations as adjuncts in the nail polish, and/or dyes or pigments in colored nail polish can be used to couple light of specific frequencies or filter light at the interface. Defining such optical structures in the nail polish allows the optical system to be dissolved and re-creating as the nail grows and/or to make optical adjustments thereto.

Figure 5:
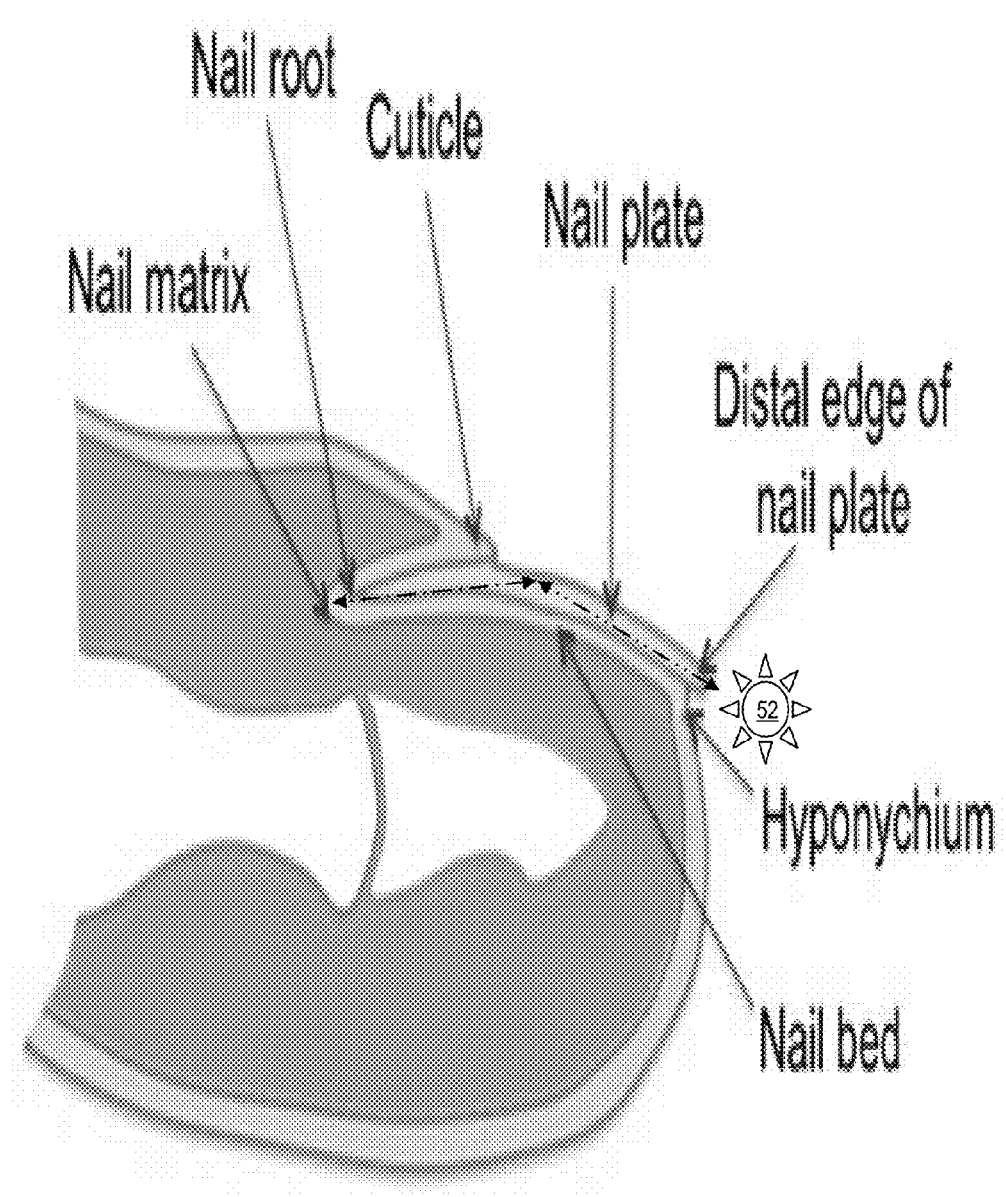
FIG. 5 depicts example optical waveguiding, according to an embodiment of the present disclosure.

FIG. 5 depicts an example 50 of optical waveguiding, according to an embodiment of the present disclosure. Light is waveguided from an external source 51 by substantially total internal reflection within the nail or a portion thereof. Optics of high efficiency, relative to the nail material itself, manage the distribution of light over the surface of the nail. For example, optical waveguides and/or diffraction gratings and other optical elements are operable for coupling the light into and out of the nail material for waveguiding to an instrument component implanted beneath the nail.

The light from the external source 51 is thus introduced into the distal end or "tip" of the nail and distributed underneath the nail cuticle to the instrument component 52 implanted there. The refractive index of the nail material exceeds that of the surrounding tissue. The light may thus be waveguided through the nail material efficiently. For example, the light may be waveguided along a path substantially parallel to a longitudinal axis of the nail that runs between the center of the tip, to the center of a line running the width of the cuticle at the opposite end of the outer surface of the nail opposite from the tip.

Blood flows through capillaries located beneath the nail. Example embodiments of the present disclosure perform various metabolic and physiological measurements over the blood flowing in the network of capillaries below the nail. An optically powered instrument component may be operable as a miniature implanted glucometer device and driven through the nail by the external light source. The glucometer may exchange optical signals through the nail with the external signal source/reader component.

Data with medical/physiological significance related to levels of various proteins may be gathered with an implanted optically powered instrument and optical signal exchange therewith from the blood flowing in the capillaries below the nail. For example, the implanted instrument component may measure levels of thrombin and other blood coagulation factors, which may be significant in administrating anticoagulants and other medications to a patient.

Implanted instrument components may also be used to monitor proteins significant to cardiovascular health. For example, detection of certain levels of some proteins such as C-reactive protein, troponin-C and β-FABP (Beta-Fatty Acid Binding Protein) by implanted instrument components may indicate approaching myocardial infarctions or other serious coronary conditions.

The implant optically powered and communicative instrument components may be implemented for measuring ion concentrations ($Cl^-$, $Na^+$, $K^+$, etc.) and levels of other blood solutes, nucleic acids (DNA, RNA) and other substances. The implant optically powered and communicative instrument components may be implemented for measuring levels of molecules in the blood that may indicate the presence or development of cancer and other diseases. Physiological stress may be studied by implementing implanted instrument components operable for measuring blood oxygenation levels, pH and $p(CO_2)$.

An example embodiment may be implemented in which the implanted instrument component is operable for performing such metabolic measurements spectroscopically, such as gathering data related to label-free refractive index or optical absorption determinations and/or Raman spectroscopy. In addition or alternatively to chemically based operability, the implanted instrument components may have electrical and/or electromagnetic operability.

An example embodiment may be implemented in which the implanted optically powered and communicative instrument component is operable for monitoring and providing excitation to nerves located underneath the nail layer. Some of the nerves below the nails (especially the fingernails) are particularly sensitive and may be stimulated by the implanted instrument components through electrophysiological excitation therewith. The implanted instrument components may also be thus operable for measuring neural action potentials and electromagnetically interrogating the nerves.

Example Biomedical Instrument System

Figure 6:
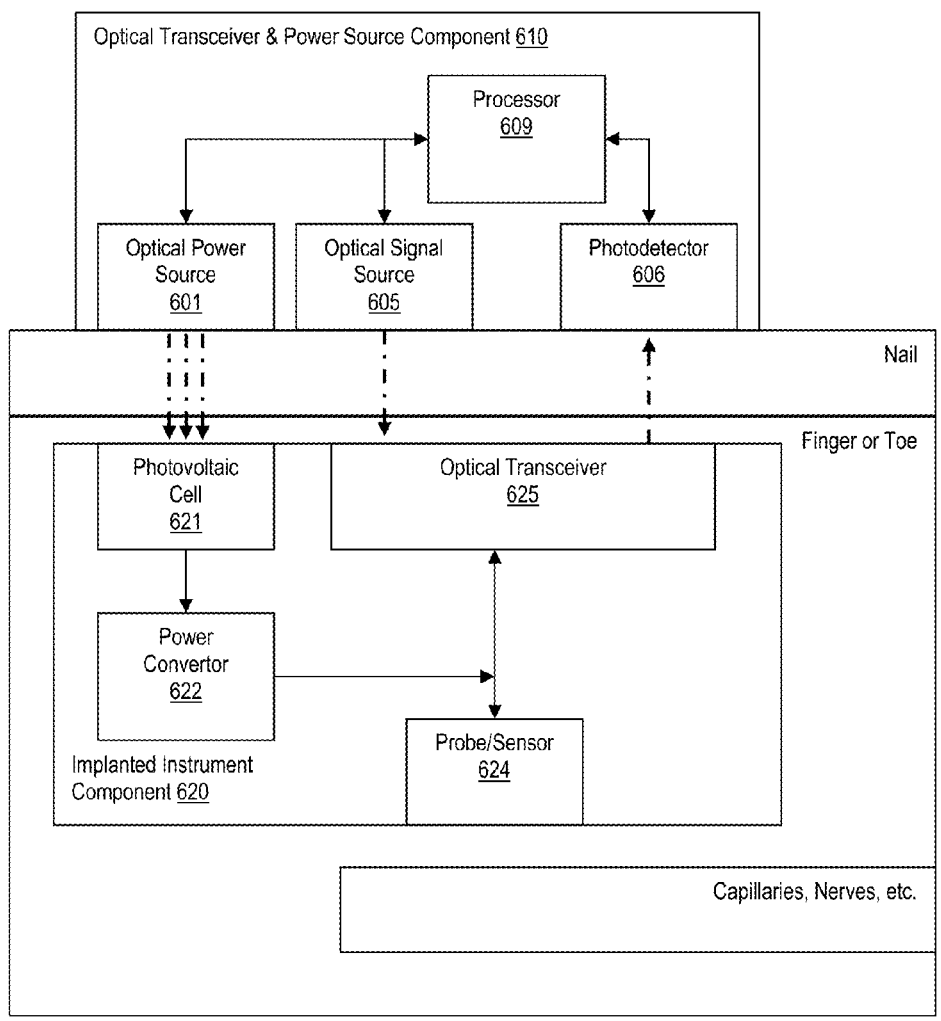
FIG. 6 depicts an example system, according to an embodiment of the present disclosure.

FIG. 6 depicts an example medical and/or physiological system 600, according to an embodiment of the present disclosure. System 600 comprises an optical transceiver and power source component 610 and an instrument component 620, which is implanted surgically below a fingernail or a toenail. The transceiver and power source component 610 is disposed above the nail and/or may be fastened thereto.

The transceiver/power source component 610 comprises an optical power source 601 such as a laser or LED and an optical signal source 605, which may dispose together as a unitary sub-component. The optical power source 601 is operable for transmitting light at infrared, visible or ultraviolet frequencies through the nail to the implanted instrument component 620 beneath it.

The light is absorbed by a photovoltaic cell 621 disposed on or near an upper surface of the implanted instrument component 620. The photocell 621 is operable for converting the absorbed optical energy to an electrical voltage, which drives a power generator 622. Driven by the voltage from the photovoltaic cell 621, the power generator 622 is operable for generating electrical power with characteristics that allow energizing a probe and/or sensor 624 and an optical transceiver 625. The probe/sensor 624 senses a characteristic of tissue beneath the nail, such as blood within capillaries or nerves disposed in the nail bed and outputs a corresponding signal to the transceiver 625.

The optical signal source 605 (which may dispose together as a unitary sub-component with the optical power source 602) is operable for transmitting optical signals at infrared, visible or ultraviolet frequencies through the nail to the implanted instrument component 620 beneath it. The optical signals are received by photoreceptor sub-components of the optical transceiver 625. Based on the received optical signals and/or an input from the probe/sensor 624, the transceiver component 625 of the implanted instrument component 620 emits an optical signal through the nail to a photosensitive detector 606 of the external transceiver/power source component 610.

An integrated processor 609 such as a microprocessor or microcontroller may receive an output of the photodetector 606 based on the optical signals received from optical transceiver 625 of the implanted instrument component 620. The processor 609 may exert corresponding or independent control over the optical signal source 605, the photodetector 606 and/or the optical power source 601.

The processor 609 may be integrated with the external transceiver/power source component 610 or may be externally coupled therewith communicatively: optically, wirelessly and/or by wireline. The implanted instrument component may optionally comprise a microprocessor or microcontroller, which exerts control over one or more of its other sub-components.

The system 600 may also comprise one or more optical structures such as a lens and/or a waveguide for coupling, focusing and/or guiding light energy through the nail in either direction between the external optical transceiver/power source component 610 and the implanted instrument component 620. Additionally, alternatively or optionally, the system 600 may also comprise one or more features described above with reference to one or more of FIG. 1 through FIG. 5, inclusive.

Not dissimilarly, the signal source 605 transmits optical signals at infrared, visible, or ultraviolet frequencies through the nail to the implanted instrument component.

Example Processes Relating to Biomedical Instrumentation

Figure 7:
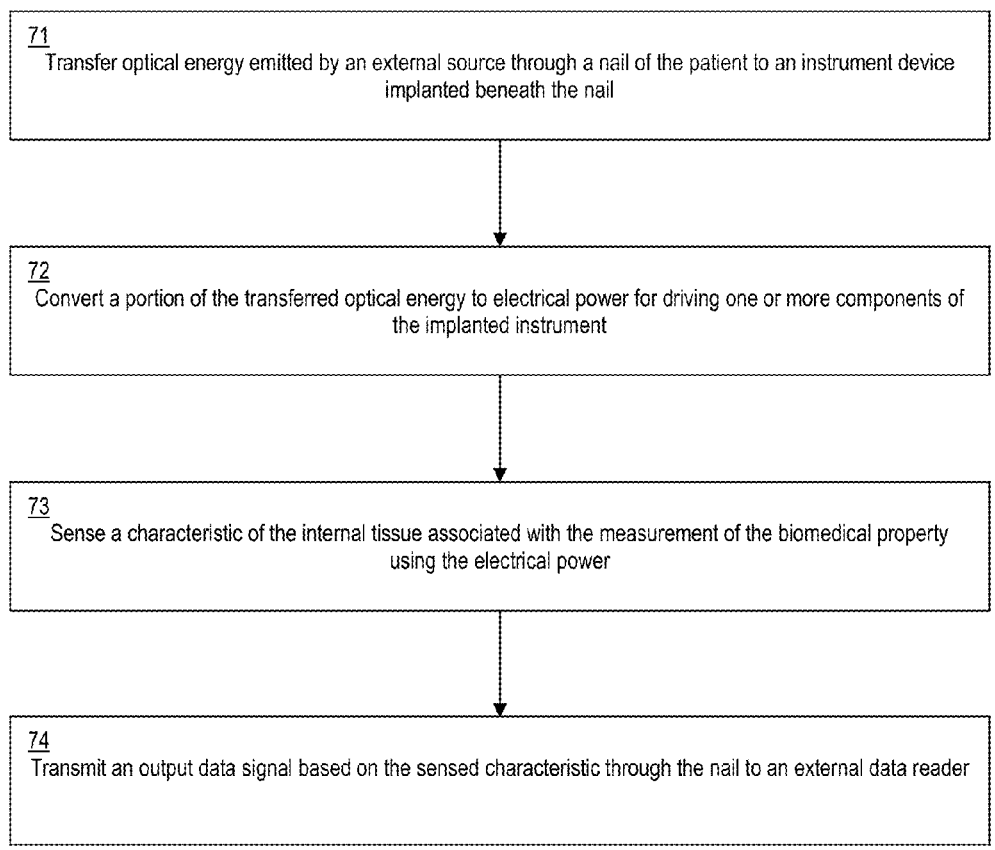
FIG. 7 depicts a flowchart for an example process for testing a biomedical property of an internal tissue of a patient, according to an embodiment of the present disclosure.

FIG. 7 depicts a flowchart for an example process 70 for testing a biomedical property of an internal tissue of a patient, according to an embodiment of the present disclosure.

In process step 71, optical energy emitted by an external source is transferred through a fingernail or toenail of the patient to an instrument device implanted beneath the nail.

In process step 72, a portion of the transferred optical energy is converted to electrical power for driving one or more components of the implanted instrument.

In process step 73, a characteristic of the internal tissue associated with the measurement of the biomedical property is sensed using the electrical power.

In process step 74, an output data signal based on the sensed characteristic is transmitted through the nail to an external data reader.

The transferred optical energy comprises, at least in part, an input data signal. The sensing of the tissue characteristic and/or transmitting the output signal may be performed responsive to the input data signal. The internal tissue may include blood within a capillary or a nerve beneath the nail.

The sensed characteristic may relate to a metabolic, electrolytic, nutritional, developmental, pharmacological, physiological, biological, experimental and/or pathological condition of the patient. The sensing of the characteristic of the internal tissue may include examining the blood tissue spectroscopically.

The instrument device may be implanted beneath the nail by injection or by surgically incising an access in the nail, inserting the instrument device through the surgical incision; and aligning the instrument device optically with the external light source.

FIG. 8 depicts a flowchart for an example surgical procedure 80 for placing a biomedical instrument within the body of a patient, according to an embodiment of the present disclosure.

In surgical procedure step 81, an access is opened through a nail of the finger or toe patient to a nail bed beneath the nail, wherein a capillary carrying blood and a nerve is disposed with the nail bed.

In surgical procedure step 82, the biomedical test instrument is implanted below the nail via the opened access, wherein the test instrument is placed in proximity with the nail bed. The biomedical test instrument is operable for sensing a biomedical characteristic of the blood or the nerve and for transmitting an output optical data signal back out through the nail based on the sensed biomedical characteristic to an optical data reader, which is disposed external to the body of the patient.

Moreover, the implanted biomedical test instrument is configured for converting optical energy received through the nail from a light source, which is disposed external to the body of the patient, into power for electrically driving the sensing of the biomedical characteristic and the transmitting the output signal.

The biomedical test instrument may be implanted by injecting the biomedical test instrument below a lower inner surface of the nail through the surgically opened access.

In an optional surgical procedure step 83, a passive optical device is installed onto an upper outer surface of the nail for directing the optical energy from the external light source to the implanted biomedical device through the nail.

The passive optical device may be disposed at least partially within the nail. The installation thereof in step 83 may thus involve altering at least a portion of the nail to accommodate the passive optical device. The passive optical device may include a lens, a diffraction grating, and/or a waveguide. The alteration of the nail portion may include controllably machining, grinding, cutting, lasing, burning, shaping, fusing, adulterating (e.g. with additives such as grits, pigments, dyes, and/or quantum dots, etc.), burnishing, polishing, augmenting, moving, clarifying, glazing, adjusting or softening material within the nail portion.

FIG. 9 depicts a flowchart for an example process 90 for energizing a biomedical instrument disposed within the body of a patient, according to an embodiment of the present disclosure.

In process step 91, transferring optical energy emitted by an external source through a nail of the patient to the biomedical instrument device, wherein the instrument device is implanted beneath the nail.

In process step 92, the optical energy absorbed by the implanted biomedical instrument device is converted to electrical power. Energized by the electrical power, the biomedical instrument is operable for sensing a characteristic of a tissue of the patient and for transmitting an optical output signal based on the sensed tissue characteristic, which is transferred back out through the nail to an external reader.

Figure 10:
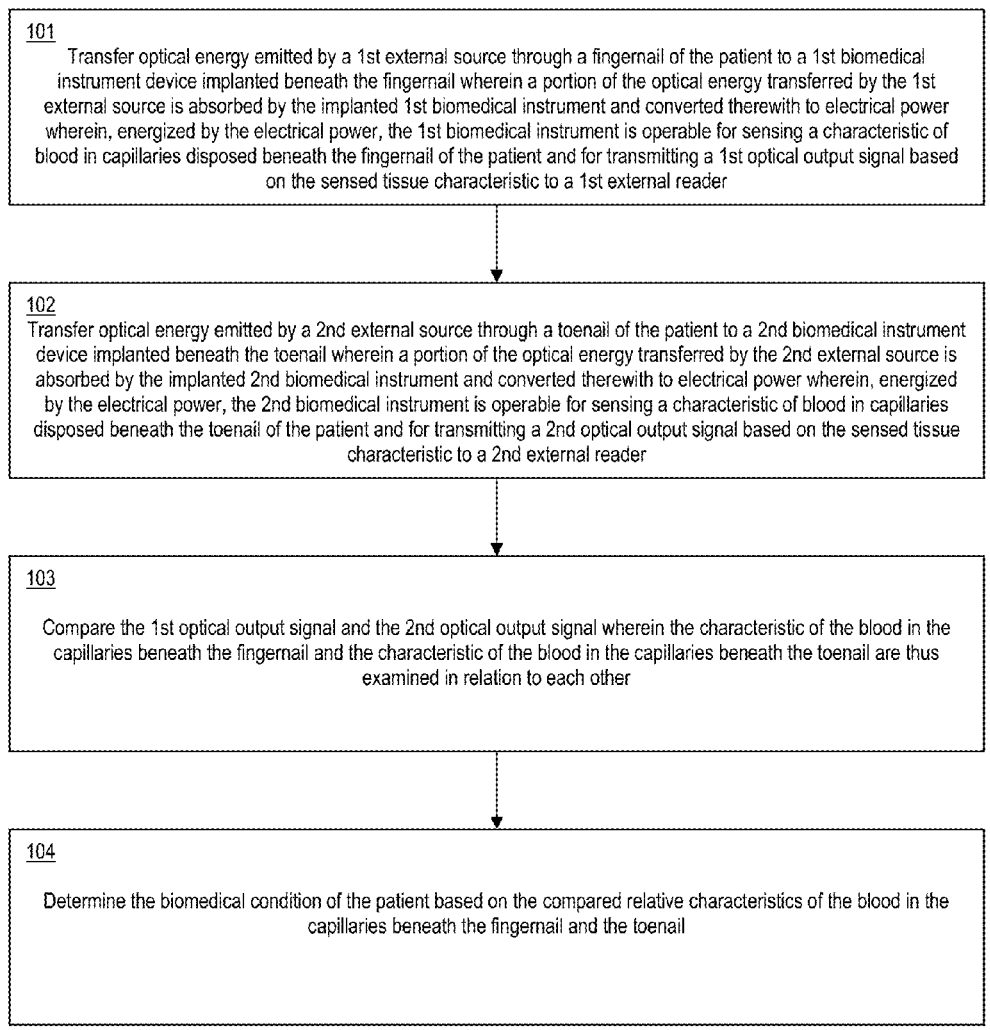
FIG. 10 depicts a flowchart for an example process for monitoring a biomedical condition of a patient, according to an embodiment of the present disclosure.

FIG. 10 depicts an example process 100 monitoring a biomedical condition of a patient. In process step 101, optical energy emitted by a first external source is transferred through a fingernail of the patient to a first biomedical instrument device implanted beneath the fingernail.

A portion of the optical energy transferred from the first external source through the fingernail is absorbed by the implanted first biomedical instrument and converted photovoltaically therewith to electrical power. Energized by the electrical power, the first biomedical instrument is operable for sensing a characteristic of blood in capillaries disposed beneath the fingernail of the patient and for transmitting a first optical output signal based on the sensed tissue characteristic, which is transferred back out through the nail to a first external reader.

In process step 102, optical energy emitted by a second external source is transferred through a toenail of the patient to a second biomedical instrument device implanted beneath the toenail.

A portion of the optical energy transferred from the second external source through the toenail is absorbed by the implanted second biomedical instrument and converted photovoltaically therewith to electrical power. Energized by the electrical power, the second biomedical instrument is operable for sensing a characteristic of blood in capillaries disposed beneath the toenail of the patient and for transmitting a second optical output signal based on the sensed tissue characteristic, which is transferred back out through the nail to a second external reader.

An example embodiment may be implemented in which the first external reader and the second external reader comprise a single unitary reader component, which may receive each of the first optical output and the second optical output as distinguishably and identifiably separate, independent or multiplexed input signals. The first optical output and the second optical output may thus be transmitted to the unitary external reader via separate optical conduits, which may be optically coupled between the upper outer surface of each of the toenails and fingernails and an input port of the external reader.

In process step 103, the first optical output signal and the second optical output signal are compared. The characteristic of the blood in the capillaries beneath the fingernail and the characteristic of the blood in the capillaries beneath the toenail are thus examined in relation to each other.

In process step 104, the biomedical condition of the patient based on the compared relative characteristics of the blood in the capillaries beneath the fingernail and the toenail. An example embodiment may be implemented in which the monitoring of the biomedical condition of the patient relates to detecting and/or measuring metabolites in the blood with Raman or other spectroscopic techniques, to track the condition and progress of metabolism and disease conditions related thereto such as diabetes, the initiation and/or development of diabetic conditions, observing and/or controlling blood transfusions, and keeping watch over circulation for anaesthetized surgical patients and comatose or otherwise immobile patients.

Example embodiments of the present disclosure are thus described in relation to providing power to medical and physiological instruments and exchanging signals therewith.

An example embodiment uses light at optical (infrared, visible, ultraviolet) wavelengths as an information and power transfer medium for medical and physiological instrumentation devices implanted within a patient or physiological specimen.

Photovoltaically driven power generator components provide energy for operating electronic circuits, other optically driven components such as micro- and nanomachines, implanted secondary optical sources, spectroscopy systems, glucometers and other biomedical instruments operable for gathering medical, hematological, pharmaceutical, physiological and biochemical (individually and collectively "biomedical" herein) data from within a patient or specimen.

Light energy is provided from an external light source to a wireless sensor implanted within the patient without optical absorption or scattering over its path at levels sufficient to undo its transfer.

An example embodiment described herein relates to a process method for testing a biomedical property of an internal tissue of a patient. Optical energy emitted by an external source is transferred through a fingernail or a toenail of the patient to an instrument device implanted beneath the nail.

A portion of the transferred optical energy is converted to electrical power for driving one or more components of the implanted instrument. A characteristic of the internal tissue associated with the measurement of the biomedical property is sensed using the electrical power. An output optical data signal based on the sensed characteristic is transmitted through the nail to an external data reader.

An example embodiment described herein relates to a system for testing a biomedical property of an internal tissue of a patient. The system includes an external light source component operable for emitting of optical energy into a fingernail or a toenail of the patient. An instrument component, which is implanted beneath the nail, is optically coupled at least partially through the nail to the external light source component.

The implanted instrument component is operable for converting a portion of the emitted optical energy into electrical power. Using the electrical power, the implanted instrument component senses a characteristic of the internal tissue associated with the measurement of the biomedical property and transmits an output optical data signal based on the sensed characteristic through the nail to an external optical data reader.

An example embodiment described herein relates to a surgical procedure for placing a biomedical test device within a body of a patient. The surgical procedure includes opening an access through a nail of the patient to a nail bed beneath the nail. A nerve and a capillary carrying blood are disposed in, or proximate to, the nail bed.

The biomedical test instrument is implanted below the nail via the opened access. The test instrument is thus placed in proximity with the nail bed, where it is operable for sensing a biomedical characteristic of the blood or the nerve. The test instrument is further operable for transmitting an output optical data signal based on the sensed biomedical characteristic to an optical data reader, which is disposed external to the body of the patient.

The implanted biomedical test instrument is configured for converting optical energy received through the nail from a light source, which is disposed external to the body of the patient, into power for driving the sensing of the biomedical characteristic and the transmission of the optical output signal.

A passive optical device may also thus be installed onto an upper outer surface of the nail. The passive optical device may include a lens, a waveguide and/or a diffraction grating, as well as an optical interface. The passive optical device directs the optical energy from the external light source to the implanted biomedical device through the nail and/or the transmitted optical signals, which have passed out through the nail to the external reader.

An example embodiment described herein relates to a process for energizing a biomedical instrument device, which is disposed within the body of a patient. Optical energy emitted by an external source through a nail of the patient to the biomedical instrument device, wherein the instrument device is implanted beneath the nail.

The optical energy absorbed by the implanted biomedical instrument device is converted therewith to electrical power. Energized by the electrical power, the biomedical instrument is operable for sensing a characteristic of a tissue of the patient and for transmitting an optical output signal based on the sensed tissue characteristic back through the nail to an external reader.

An example embodiment described herein relates to a biomedical instrument device configured to be implanted within the body of a patient. The device has a power conversion component operable for converting optical energy received through a nail of the patient to electrical power.

A sensor component of the device is energized by the electrical power and is operable for sensing a characteristic of a tissue of the patient disposed beneath the nail. A transmitter component energized by the electrical power is operable for transmitting an optical output signal, based on the sensed tissue characteristic, through the nail to an external reader.

An example embodiment described herein relates to a method for monitoring a biomedical condition of a patient. Optical energy emitted by a first external source is transferred through a fingernail of the patient to a first biomedical instrument device implanted beneath the fingernail. A portion of the optical energy transferred by the first external source is absorbed by the implanted first biomedical instrument and converted photovoltaically therewith to electrical power.

Energized by the electrical power, the first biomedical instrument is operable for sensing a characteristic of blood in capillaries disposed beneath the fingernail of the patient and for transmitting a first optical output signal based on the sensed tissue characteristic to a first external reader.

Optical energy emitted by a second external source is transferred through a toenail of the patient to a second biomedical instrument device implanted beneath the toenail. A portion of the optical energy transferred by the second external source is absorbed by the implanted second biomedical instrument and converted therewith photovoltaically to electrical power.

Energized by the electrical power, the second biomedical instrument is operable for sensing a characteristic of blood in capillaries disposed beneath the toenail of the patient and for transmitting a second optical output signal based on the sensed tissue characteristic to a second external reader.

The first optical output signal and the second optical output signal are compared. The characteristic of the blood in the capillaries beneath the fingernail and the characteristic of the blood in the capillaries beneath the toenail are thus examined in relation to each other.

Based on the compared relative characteristics of the blood in the capillaries beneath the fingernail and the toenail, the biomedical condition of the patient is determined.

Example embodiments of the present disclosure are thus described in relation to providing power to medical and physiological instruments and exchanging signals therewith. An example embodiment uses light at optical (infrared, visible, ultraviolet) wavelengths as an information and power transfer medium for medical and physiological instrumentation devices implanted within a patient or physiological specimen.

Photovoltaically driven power generator components provide energy for operating electronic circuits, other optically driven components such as micro- and nanomachines, implanted secondary optical sources, spectroscopy systems, glucometers and other biomedical instruments operable for gathering medical, hematological, pharmaceutical, physiological and biochemical (individually and collectively "biomedical" herein) data from within a patient or specimen.

Light energy is provided from an external light source to a wireless sensor implanted within the patient without optical absorption or scattering over its path at levels sufficient to undo its transfer.

An example embodiment of the present disclosure is described above in relation to a process for testing a biomedical property of an internal tissue of a patient. Optical energy emitted by an external source is transferred through a nail of the patient to an instrument device implanted beneath the nail. A portion of the transferred optical energy is converted to electrical power for driving components of the implanted instrument. Using the electrical power, a characteristic of the internal tissue associated with the measurement of the biomedical property is sensed and an output data signal based on the sensed characteristic is transmitted through the nail to an external data reader.

Definitions that are expressly set forth in each or any claim specifically or by way of example herein, for terms contained in relation to features of such claims are intended to govern the meaning of such terms. Thus, no limitation, element, property, feature or attribute that is not expressly recited in a claim should limit the scope of such claim in any way. The specification and drawings are, accordingly, to be regarded in an illustrative rather than a restrictive sense. Example embodiments of the present disclosure relate to providing power to medical and physiological instruments and exchanging signals therewith.

What is claimed is:

1. A method for testing a biomedical property of an internal tissue of a patient, the method comprising:
    transferring optical energy emitted by an optical power source and an optical signal source through a nail of the patient to an instrument device implanted beneath the nail;
    converting a portion of the transferred optical energy from the optical power source to electrical power for driving one or more components of the implanted instrument;

sensing a characteristic of the internal tissue associated with the measurement of the biomedical property using the electrical power; and using the transferred optical energy from the optical signal source for transmitting an output data signal based on the sensed characteristic through the nail to an external data reader.

2. The method as recited in claim 1 wherein transferring optical energy emitted by the optical signal source comprises, at least in part, providing an input data signal.

3. The method as recited in claim 2 wherein one or more of the sensing the tissue characteristic or the transmitting the output signal is performed responsive to the input data signal.

4. The method as recited in claim 1 wherein the sensing the characteristic of the internal tissue comprises sensing blood within a capillary beneath the nail.

5. The method as recited in claim 4 wherein sensing the characteristic of the internal tissue relates to one or more of a metabolic, electrolytic, nutritional, developmental, pharmacological, physiological, biological, experimental, or pathological condition of the patient.

6. The method as recited in claim 4 wherein the sensing the characteristic of the internal tissue comprises examining the blood tissue spectroscopically.

7. The method as recited in claim 1 wherein sensing the characteristic of the internal tissue relates to a nerve beneath the nail.

8. The method as recited in claim 1 further comprising implanting the instrument device beneath the nail.

9. The method as recited in claim 8 wherein the implanting comprises injecting the instrument beneath the nail.

10. The method as recited in claim 8 wherein the implanting comprises:
surgically incising an access in the nail;
inserting the instrument device through the surgical incision; and
aligning the instrument device optically with the external light source.

11. A system for testing a biomedical property of an internal tissue of a patient, the system comprising:
an external light source component configured for emitting of optical energy from an optical power source and from an optical signal source into a nail of the patient; and
an instrument component configured for being implanted beneath the nail and configured for being optically coupled at least partially through the nail to the external light source component wherein the implanted instrument component is further configured for
converting a portion of the emitted optical energy from the optical power source into electrical power,
sensing a characteristic of the internal tissue associated with the measurement of the biomedical property using the electrical power, and
using the emitted optical energy from the optical signal source for transmitting an output optical data signal based on the sensed characteristic through the nail to an external optical data reader.

12. The system as recited in claim 11 wherein the emitted optical signal source is configured as, at least in part, an input data signal.

13. The system as recited in claim 12 wherein the implanted instrument component is configured to perform one or more of the sensing the tissue characteristic or the transmitting the output signal in response to receiving the input data signal.

14. The system as recited in claim 11 wherein the implanted instrument component is configured to sense internal tissue comprising blood within a capillary beneath the nail.

15. The system as recited in claim 14 wherein the implanted instrument component is configured to sense a characteristic of the blood associated with one or more of a metabolic, electrolytic, nutritional, developmental, pharmacological, physiological, biological, experimental or pathological condition of the patient.

16. The system as recited in claim 14 wherein the implanted instrument component is configured to provide the sensing the characteristic of the internal tissue for examining the blood tissue spectroscopically.

17. The system as recited in claim 11 wherein the implanted instrument component is configured to sense a nerve beneath the nail.

18. The system as recited in claim 17 wherein the external light source component is configured to be disposed above the upper outer surface of the nail in a first position based on an initial optical alignment with the instrument component implanted beneath the nail.

19. The system as recited in claim 18 wherein, as the nail grows, the external light source component is configured to be moved to at least a second position above the upper outer surface of the nail wherein the external light source is configured to maintain the optical alignment with the instrument component implanted beneath the nail.

20. The system as recited in claim 11 further comprising a passive optical component operable for optically coupling the emitted optical energy from the external light source to the implanted instrument component system.

21. The system as recited in claim 20 wherein the passive optical component comprises a lens and wherein the optical coupling is configured for focusing the emitted optical energy.

22. The system as recited in claim 20 wherein the passive optical component comprises a waveguide and wherein the optical coupling is configured for directing the path of the emitted optical energy.

23. The system as recited in claim 20 wherein the passive optical component is configured to be disposed upon a surface of the nail.

24. The system as recited in claim 20 wherein the passive optical component is configured to be disposed at least partially within the nail.

25. The system as recited in claim 20 wherein the optical coupling the emitted optical energy from the external light source to the implanted instrument component system is configured for coupling the emitted optical energy through the passive optical component into the nail.

26. The system as recited in claim 20 wherein the passive optical component comprises a substantially transparent nail polish.

27. The system as recited in claim 26 wherein the passive optical component further comprises a material disposed within the nail polish configured for filtering the emitted optical energy in relation to a frequency related characteristic thereof.

28. The system as recited in claim 27 wherein the material disposed within the nail polish configured for filtering the emitted optical energy comprises one or more of a grit, a pigment, a dye or a quantum dot.

29. The system as recited in claim 11 wherein the external light source component is configured to be disposed above an upper outer surface of the nail.

30. The system as recited in claim 29 wherein the external light source component is configured to be affixed to the upper outer surface of the nail.

31. A surgical method for placing a biomedical test instrument within a body of a patient, the surgical method comprising:
   opening an access through a nail of the patient to a nail bed beneath the nail,
      wherein the nail bed comprises a capillary carrying blood and a nerve; and
   implanting the biomedical test instrument below the nail via the opened access,
      wherein the test instrument is placed in proximity with the nail bed and operable for sensing a biomedical characteristic of the blood or the nerve and transmitting an output optical data signal based on the sensed biomedical characteristic through the nail to an optical data reader, which is disposed external to the body of the patient, and
      wherein the implanted biomedical test instrument is configured to receive an optical power source signal and an optical signal source signal and configured for converting optical energy received through the nail from the optical power source, which is disposed external to the body of the patient, into power for driving the sensing the biomedical characteristic and the optical signal source signal is used for transmitting the output signal.

32. The surgical method as recited in claim 31 wherein the implanting the biomedical test instrument comprises injecting the biomedical test instrument below a lower inner surface of the nail.

33. The surgical method as recited in claim 31, further comprising installing a passive optical device onto an upper outer surface of the nail for directing the optical energy from the external light source to the implanted biomedical device through the nail.

34. The surgical method as recited in claim 33 wherein the passive optical device is disposed at least partially within the nail and wherein the installing the passive optical device comprises altering at least a portion of the nail to accommodate the passive optical device.

35. The surgical method as recited in claim 34 wherein the passive optical device comprises one or more of a lens, a waveguide, a diffraction grating or a prism.

36. The surgical method as recited in claim 34 wherein the altering the nail portion comprises one or more of controllably machining, grinding, cutting, lasing, burning, shaping, fusing, adulterating, burnishing, polishing, augmenting, moving, clarifying, glazing, adjusting or softening material within the nail portion.

37. A method for energizing a biomedical instrument device disposed within the body of a patient, the method comprising:
   transferring optical energy emitted by an external optical power source and an external optical signal source through a nail of the patient to the biomedical instrument device, wherein the instrument device is implanted beneath the nail; and
   converting the optical energy from the optical power source absorbed by the implanted biomedical instrument device to electrical power wherein, energized by the electrical power, the biomedical instrument is operable for sensing a characteristic of a tissue of the patient and using the optical energy from the optical signal source for transmitting an optical output signal based on the sensed tissue characteristic through the nail to an external reader.

38. A biomedical instrument device configured to be implanted within the body of a patient, the device, comprising:
   a power conversion component configured for converting optical energy received from an external optical power source through a nail of the patient to electrical power;
   a sensor component energized by the electrical power and operable for sensing a characteristic of a tissue of the patient disposed beneath the nail; and
   a transmitter component configured to receive an external optical input signal from an external signal source and operable for transmitting an optical output signal, based on the sensed tissue characteristic, through the nail to an external reader.

39. A method for monitoring a biomedical condition of a patient, the method comprising:
   transferring optical energy emitted by a first external optical power source and a first external optical signal source through a fingernail of the patient to a first biomedical instrument implanted beneath the fingernail wherein a portion of the optical energy transferred by the first external optical power source is absorbed by the implanted first biomedical instrument and converted therewith to electrical power wherein, energized by the electrical power, the first biomedical instrument is operable for sensing a characteristic of blood in capillaries disposed beneath the fingernail of the patient and for using the first external optical signal for transmitting a first optical output signal based on the sensed tissue characteristic through the fingernail to a first external reader;
   transferring optical energy emitted by a second external optical power source and a second external optical signal source through a toenail of the patient to a second biomedical instrument implanted beneath the toenail wherein a portion of the optical energy transferred by the second external optical power source is absorbed by the implanted second biomedical instrument and converted therewith to electrical power wherein, energized by the electrical power, the second biomedical instrument is operable for sensing a characteristic of blood in capillaries disposed beneath the toenail of the patient and for using the second external optical signal for transmitting a second optical output signal based on the sensed tissue characteristic through the toenail to a second external reader;
   comparing the first optical output signal and the second optical output signal wherein the characteristic of the blood in the capillaries beneath the fingernail and the characteristic of the blood in the capillaries beneath the toenail are examined in relation to each other; and
   determining the biomedical condition of the patient based on the compared relative characteristics of the blood in the capillaries beneath the fingernail and the toenail.

* * * * *